United States Patent [19]

Kawamura et al.

[11] Patent Number: 6,134,341
[45] Date of Patent: Oct. 17, 2000

[54] METHOD FOR ANALYZING A STEREOSCOPIC IMAGE OF A FUNDUS, AND AN APPARATUS FOR EXECUTING THAT METHOD

[75] Inventors: Masunori Kawamura; Manabu Noda; Tsuguo Nanjo, all of Aichi, Japan

[73] Assignee: Nidek Co., Ltd., Aichi, Japan

[21] Appl. No.: 08/984,535

[22] Filed: Dec. 3, 1997

[30] Foreign Application Priority Data

Dec. 3, 1996 [JP] Japan .................................... 8-339078

[51] Int. Cl.$^7$ ................................ G06K 9/00; A61B 3/10
[52] U.S. Cl. ........................................... 382/128; 351/200
[58] Field of Search ................................... 382/128, 199; 351/200, 205, 210

[56] References Cited

FOREIGN PATENT DOCUMENTS

| 7-136121 | 5/1995 | Japan | A61B 3/12 |
| 8-567 | 1/1996 | Japan | A61B 3/14 |
| WO 94/23641 | 10/1994 | WIPO | A61B 3/10 |

OTHER PUBLICATIONS

"Stereo Measurement of the Ocular Fundus in Ophthalmology", T. Takamoto et al., Proceedings Of SPIE, vol 361, Aug. 24–27, 1982, San Diego, pp. 324–329, XP002060643.

"Topographic Analysis of Ocular Fundus Using the Fourier Transform Method for Projected Grating Images", T. Yoshimura et al., Optical Review, vol.42, No. 5, 1995, pp. 388–393, XP002060644.

"Integrating Stereo and Photometric Stereo to Monitor the Development of Glaucoma", Lee et al., Image and Vision Computing, vol. 9, No. 1, Feb. 1991, pp. 39–44, XP002060645.

*Primary Examiner*—Matthew Bella
*Attorney, Agent, or Firm*—Sughrue, Mion, Zinn, Macpeak & Seas, PLLC

[57] ABSTRACT

A method for analyzing a stereoscopic image of a fundus to detect and analyze an optic disk part on the basis of the stereoscopic image of the fundus, which can provide highly reliable results of analysis even if the fundus is inclined. The method includes: a first step of designating a disk line in the stereoscopic image of the fundus; a second step of determining a lowest point in a disk region which is determined by the designated disk line; a third step of determining a cross section of the disk region at each predetermined angle centering on the lowest point; a fourth step of determining highest points at both ends of a line of longitude on each cross section of the disk region; a fifth step of setting as a cup point a level which is lower from the highest points by a predetermined depth; and a sixth step of forming a cup rim by consecutively connecting the cup points in the cross sections of the disk region determined in the fifth step.

17 Claims, 5 Drawing Sheets

METHOD FOR ANALYZING A STEREOSCOPIC IMAGE OF A FUNDUS, AND AN APPARATUS FOR EXECUTING THAT METHOD

BACKGROUND OF THE INVENTION

The present invention relates to a method for analyzing a stereoscopic image of a fundus to detect and analyze the optic disk on the basis of the stereoscopic image of the fundus, and an apparatus for executing that method.

Glaucoma is known as a disease of the visual function. In the examination of glaucoma, it is said that the observation of patient's optic disk on the basis of an image of the fundus is important. In recent years, it has become possible to quantitatively measure the optic disk due to progress in the technology of image analysis. As the results of analysis, the following parameters are computed: the C/D ratio (a distance ratio between a rim of an optic disk cupping (the optic disk cupping being referred to as a cup) and a rim of the optic disk (the optic disk being referred to as a disk)), the area of the plane within the cup rim, the depth of the cup, the volume of the cup, and the like.

The rim of the cup which serves as a basis for the computation of these parameters is conventionally detected such that, by using the disk as a reference, positions which are lowered by an arbitrary depth (e.g., 150 $\mu$m) from the disk are estimated to plot the rim of the cup.

However, since it is not uncommon that overall disk regions of the patent's eyes are inclined, there arise cases where the rim of the cup cannot be detected by the above-described detection method.

It is possible to obviate the above-described problem if an operator designates three points on the disk region and effects analysis by using as a reference plane an inclined plane thus determined. In accordance with this method, however, there is a problem in that the data of the cups detected vary for each operator, and the data can be different on each occasion of analysis even for the same operator, with the result that the reliability and reproducibility of the results of analysis are poor.

SUMMARY OF THE INVENTION

In view of the above-described problems of the conventional art, a technical task of the present invention is to provide a method and an apparatus for analyzing a stereoscopic image of the fundus which make it possible to obtain highly reliable results of analysis even if the fundus is inclined and which give excellent reproducibility.

To overcome the above-described problems, the present invention is characterized by the following features.

(1) A method for analyzing a stereoscopic image of a fundus to detect and analyze an optic disk on the basis of the stereoscopic image of the fundus, the method comprising:
- a first step of designating a disk line in the stereoscopic image of the fundus;
- a second step of determining a lowest point in a disk region which is determined by the designated disk line;
- a third step of determining a cross section of the disk region at each predetermined angle centering on the lowest point in the disk region;
- a fourth step of determining highest points at both ends of a line of longitude on each cross section of the disk region;
- a fifth step of setting, as cup points in each cross section, points existing on the line of longitude and on levels which are respectively lower from the highest points by a predetermined depth; and
- a sixth step of forming a cup rim by consecutively connecting the thus set cup points in all cross sections.

(2) A method for analyzing a stereoscopic image of a fundus according to (1), wherein said second step includes:
- a step of determining a first tentative central position in the disk region determined by the disk line designated in said first step;
- a step of determining a first cross section of the disk region at each predetermined angle centering on the first tentative central position;
- a step of determining a lowest point in each of the first cross sections of the disk region; and
- a step of determining a lowest point in the disk region among the lowest points determined in the respective first cross sections of the disk region. (3) A method for analyzing a stereoscopic image of a fundus according to (2), further comprising:
- a step of determining a second cross section of the disk region at each predetermined angle centering on the lowest point in the disk region among the lowest points determined in the respective first cross sections;
- a step of determining a lowest point in each of the second cross section of the disk region; and
- a step of determining a lowest point in the disk region among the lowest points determined in the respective second cross sections of the disk region.

(4) A method for analyzing a stereoscopic image of a fundus according to (3), wherein the step of determining a second cross section of the disk region is shared with said third step.

(5) A method for analyzing a stereoscopic image of a fundus according to (1), wherein in said fifth step, if a plurality of points exists on the line of longitude and on the level lower from one of the highest points by the predetermined depth, then one of the points, which is closest to the lowest point determined in said second step, is set as the cup point.

(6) A method for analyzing a stereoscopic image of a fundus according to (1), further comprising the step of obtaining a cup plane by taking as a reference position a highest point of the cup rim as a result of comparison of the highest points determined in said fourth step and by projecting a curved surface of the cup defined by the cup rim onto a horizontal plane including the reference position.

(7) A method for analyzing a stereoscopic image of a fundus according to (1), further comprising the step of computing optic disk parameters.

(8) An apparatus for analyzing a stereoscopic image of a fundus, which has storage means for storing the method for analyzing a stereoscopic image of a fundus according to (1).

(9) An apparatus for analyzing a stereoscopic image of a fundus, which has storage means for storing the method for analyzing a stereoscopic image of a fundus according to (2).

(10) An apparatus for analyzing a stereoscopic image of a fundus, which has storage means for storing the method for analyzing a stereoscopic image of a fundus according to (3).

(11) An apparatus for analyzing a stereoscopic image of a fundus, which has storage means for storing the method for analyzing a stereoscopic image of a fundus according to (4).

(12) An apparatus for analyzing a stereoscopic image of a fundus, which has storage means for storing the method for analyzing a stereoscopic image of a fundus according to (5).

(13) An apparatus for analyzing a stereoscopic image of a fundus, which has storage means for storing the method for analyzing a stereoscopic image of a fundus according to (6).

(14) An apparatus for analyzing a stereoscopic image of a fundus, which has storage means for storing the method for analyzing a stereoscopic image of a fundus according to (7).

(15) An apparatus for analyzing a stereoscopic image of a fundus to detect and analyze an optic disk on the basis of the stereoscopic image of the fundus, the apparatus comprising:

data input means for inputting data on the stereoscopic image of the fundus;

designating means for designating a disk line in the input stereoscopic image of the fundus;

storage means for storing a program for detecting a cup rim on the basis of the designated disk line and the data on the stereoscopic image of the fundus, said program including the steps of determining a lowest point in a disk region which is determined by the designated disk line, determining a cross section of the disk region at each predetermined angle centering on the lowest point, determining highest points at both ends of a line of longitude on each cross section of the disk region, setting, as cup points in each cross section, points existing on the line of longitude and on levels which are respectively lower from the highest points by a predetermined depth, and forming a cup rim by consecutively connecting the thus set cup points in all cross sections;

program executing means for executing said program;

parameter computing means for computing predetermined parameters for analysis of the optic disk on the basis of the cup rim detected by said program executing means; and display means for displaying a result of the computation.

DETAILED DESCRIPTION OF THE PREFERRED EMBODIMENT

Figure 1:
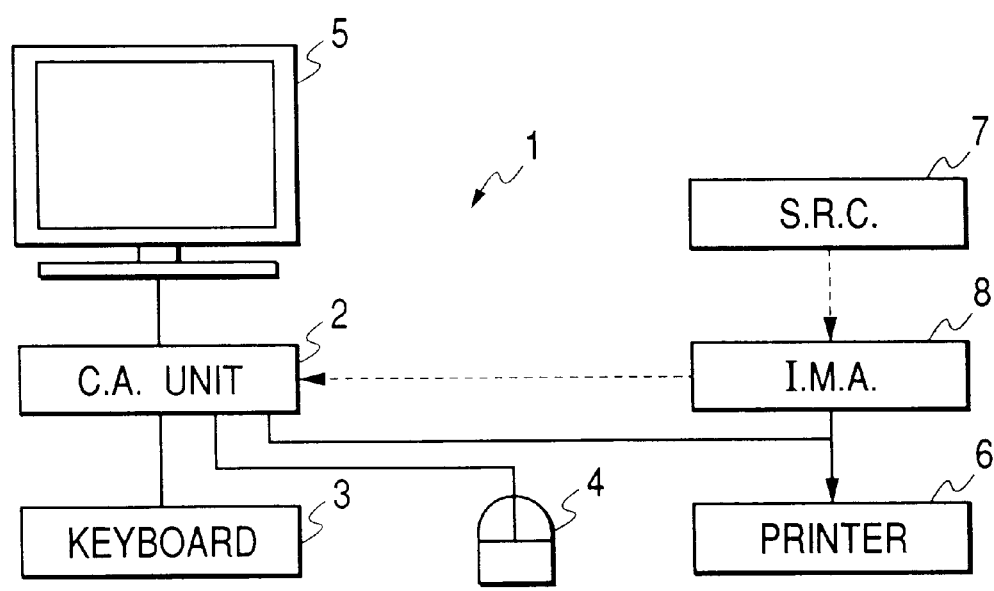
FIG. 1 is a schematic block diagram of the apparatus in accordance with an embodiment.
Figure 2:
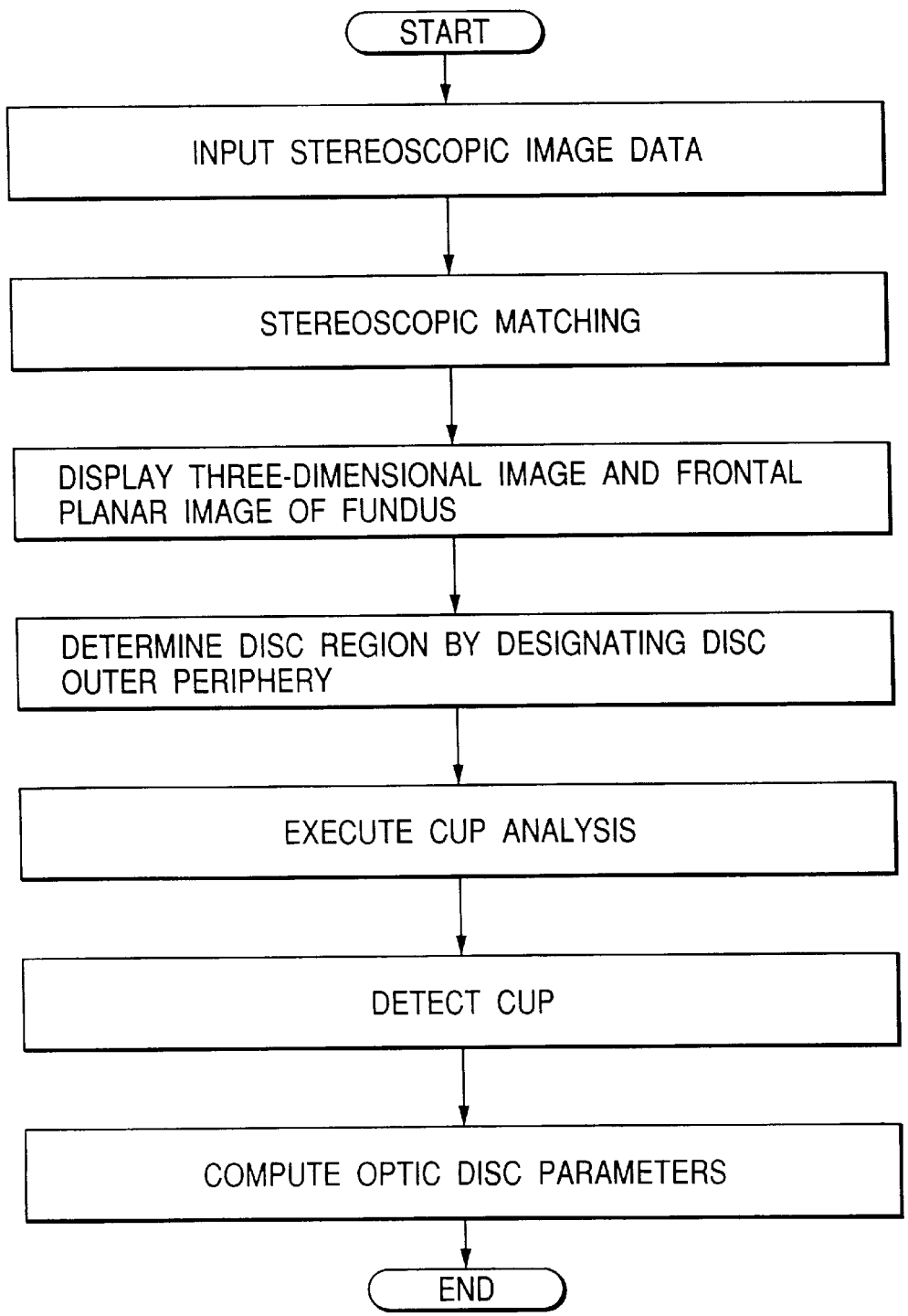
FIG. 2 is a diagram illustrating a flowchart of the overall analysis of an image of the fundus of the eye.
Figure 3:
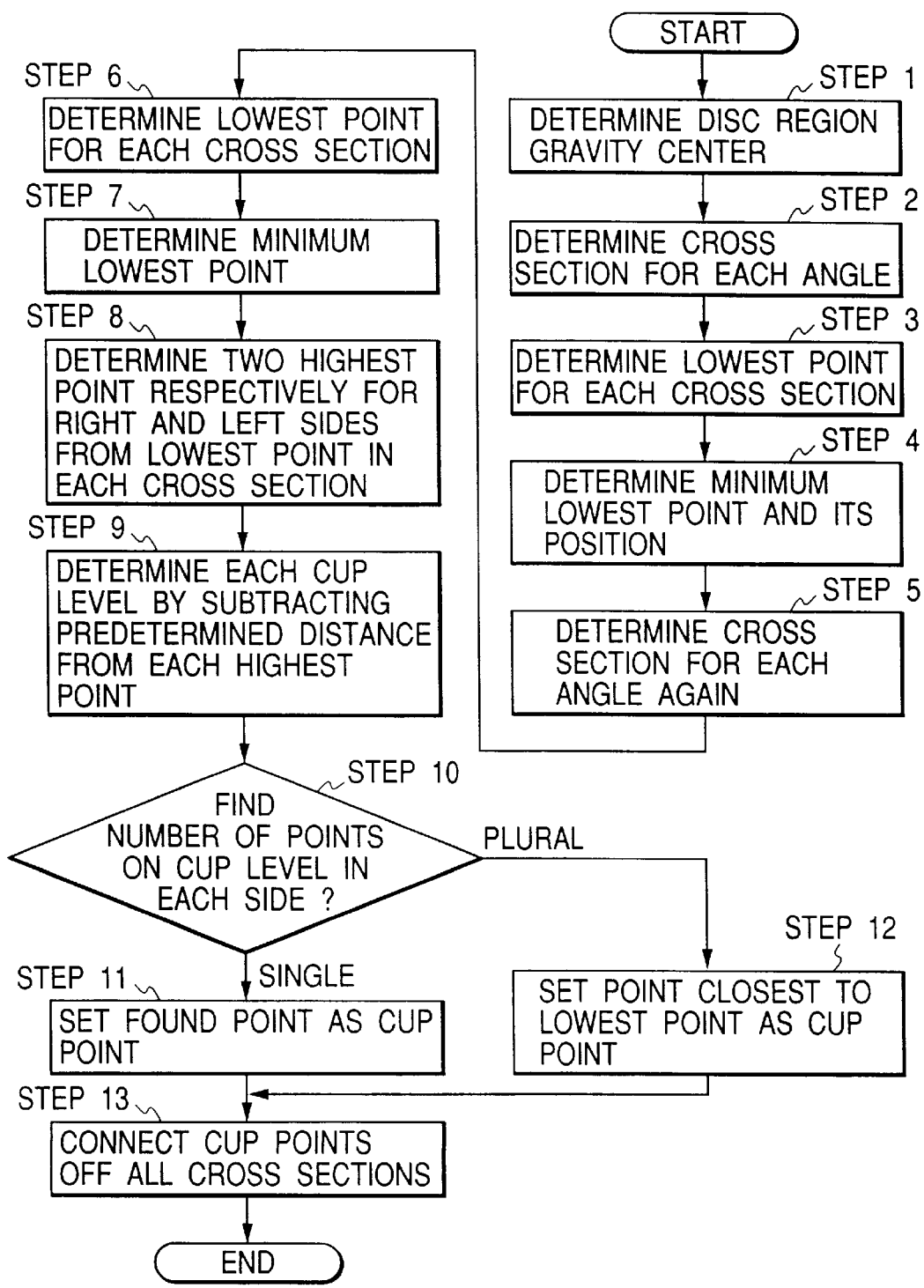
FIG. 3 is a diagram illustrating a flowchart for detecting the cup.

Referring now to the drawings, a description will be given of an embodiment of the present invention. FIG. 1 is a schematic block diagram of an apparatus in accordance with the embodiment. An analyzing apparatus 1 is comprised of a computing and analyzing unit 2, a keyboard 3 and a mouse 4 which constitute a designation input section, a display 5 for displaying an image of a fundus, the results of analysis, and the like, and a printer 6. A commercially available personal computer can be used as the analyzing unit 2. Also, commercially available ones can be used as the other component parts. Reference numeral 7 denotes a stereoscopic retinal (fundus) camera, wherein a bundle of illumination light rays reflected from the fundus is separated into two bundle of rays by a bifurcating (two-hole) diaphragm to obtain a pair of right and left stereoscopic images. The stereoscopic image of the fundus photographed by the stereoscopic retinal (fundus) camera 7 is converted into image data by an image reading apparatus 8, and is inputted to the computing and analyzing unit 2. As the stereoscopic retinal (fundus) camera 7, it is possible to use a type in which image of the fundus is photographed on a transparency film, or a type in which an image on the fundus is photographed by a CCD camera. In the case of the latter type, after the image of the fundus is recorded in an image recording means as a still picture, the image of the fundus is inputted into the computing and analyzing unit 2 directly or via a recording medium such as a floppy disk.

Next, a description will be given of the analysis of an image of the fundus by means of the computing and analyzing unit 2 (see FIGS. 2 to 5). First, a pair of stereoscopic image data of the fundus photographed by the stereoscopic retinal (fundus) camera 7 is inputted into the computing and analyzing unit 2. The computing and analyzing unit 2 incorporates correction based on a parallax, a magnification of image formation, a distortion due to aberrations and the like into the inputted stereoscopic image data, subjects the corrected stereoscopic image data to stereoscopic matching, and obtains three-dimensional data of the fundus on the basis of the same. As the stereoscopic matching, it is possible to use an apparatus disclosed in Japanese Patent Application Laid-Open No. 8-567 (Title of the Invention: Fundus Oculi Measuring Instrument).

Subsequently, an outer peripheral line of the disk is designated. On the basis of the three-dimensional data of the fundus, a bird's-eye view (or a triangular net) showing a three-dimensional image (configuration) of the fundus and a front view showing a planar image (frontal, planar configuration) of the fundus are displayed on the display 5, and the operator designates a disk region in the displayed three-dimensional image or planar image of the fundus. The designation of the disk region is effected as follows. Since a pointer for designating an outer peripheral line of the disk is displayed in the three-dimensional image and the planar image on the display 5, the pointer is moved and then the mouse 4 is clicked to designate a multiplicity of (preferably, 10 or more) points on the outer peripheral line of the disk.

After the designation of the outer peripheral line of the disk, the operator instructs the execution of cup analysis processing to the computing and analyzing unit 2. The computing and analyzing unit 2 first effects the detection of the cup. The detection of the cup is effected in accordance with the flowchart shown in FIG. 3.

The designated points are connected by a quarter spline curve in such a manner as to form a smooth line, and that line is depicted in such a manner as to be superposed on the planar image on the display 5. By depicting the designated points by the spline curve, it is possible to determine the outer peripheral line of the disk in a shape which approximates a real one very closely. In addition, it is possible to cope with even the outer periphery of the disk which has a distorted shape. The computing and analyzing unit 2 sets its inner side as the disk region, and determines the position of its center of gravity (Step 1). The position of the center of gravity serves as a tentative central position, on the basis of which the position of a lowest point within the disk region is determined.

The computing and analyzing unit 2 determines a cross section of the disk for each predetermined detection angle (e.g., for each 1 degree) by using as the center the position of the center of gravity determined in Step 1 (Step 2), and determines a lowest point (a deepest point) for each cross section of the disk (Step 3). A minimum lowest point as well as its position in the disk region are determined among the lowest points for the respective cross sections of the disk determined in Step 3 (Step 4). By using as the center the position of the minimum lowest point determined in Step 4, the cross section of the disk is determined again for each predetermined detection angle (e.g., for each 1 degree) (Step 5). Further, lowest points in the respective cross sections of the disk determined in Step 5 are determined (Step 6), and a minimum lowest point is determined among the lowest points determined in Step 6 (Step 7). This minimum lowest point determined in Step 7 approximates a true lowest point within the disk region.

Figure 4:
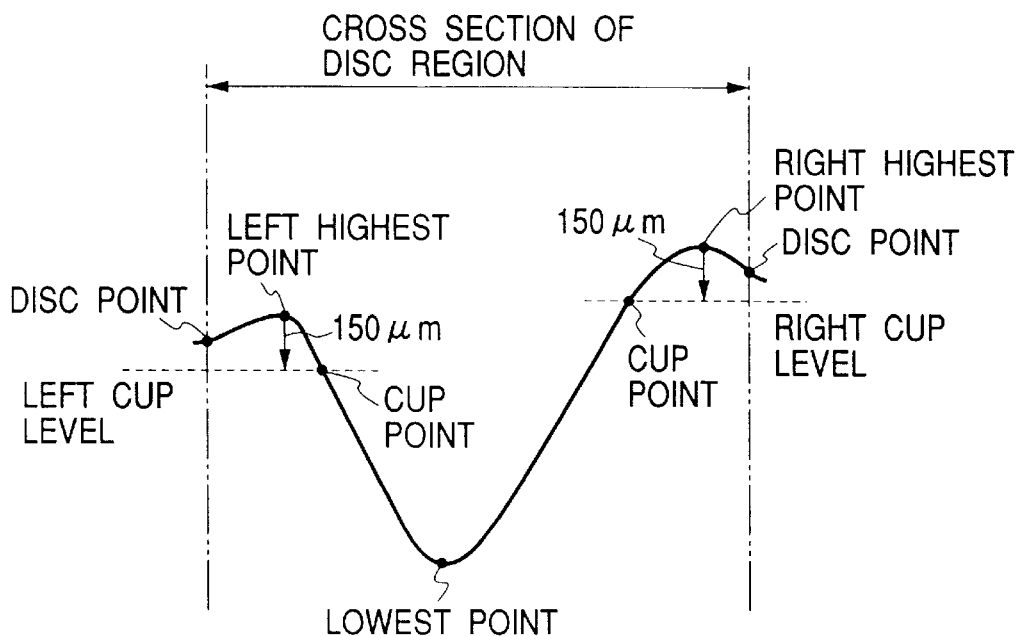
FIG. 4 is a diagram explaining the steps for determining the cup level in a cross section of the disk.
Figure 5:
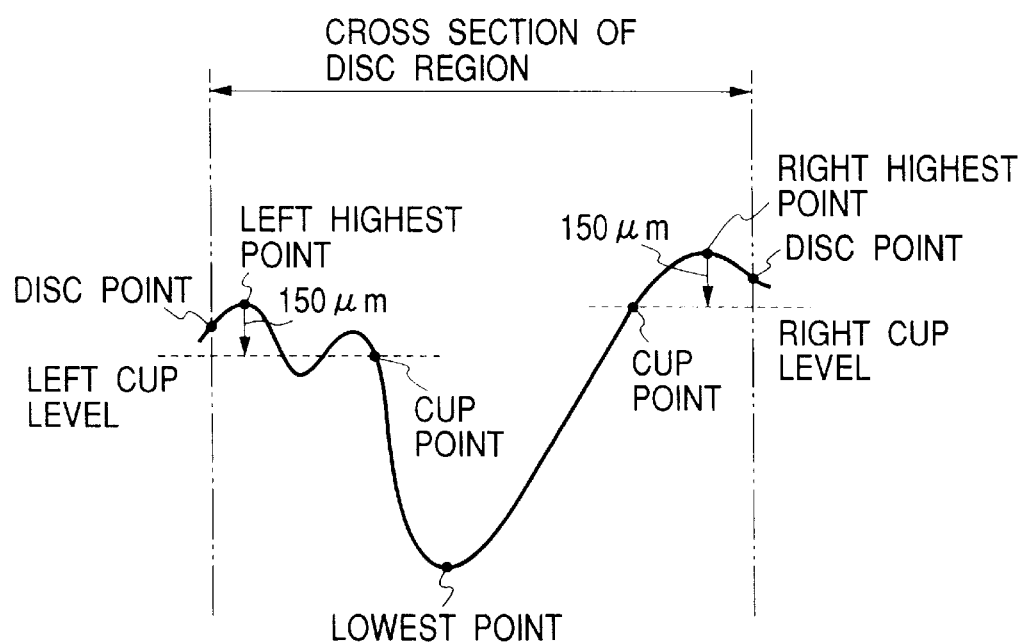
FIG. 5 is a diagram explaining a method for determining cup points when there are a plurality of points which reached the cup level.

Two highest points in both directions between the lowest point in each cross section of the disk determined in Step 6 and each of the disk point on either side (either end of the cross section of the disk) are respectively determined (Step 8), and the level which is lower from each of the determined highest points by a predetermined distance (e.g., 150 μm) is set as each cup level (Step 9, see FIG. 4).

Points on the cup level are searched in each cross section of the disk left and right directions from the lowest point determined in Step 6, the number of points which reached the cup level are found (Step 10), and if the number of points which reached the cup level is one for each of the left and right directions from the lowest point determined in Step 6, that point is set as the cup point (Step 11). When there are a plurality of points which reached the cup level, a point which is closest to the lowest point determined in Step 6 is set as the cup point (Step 12, see FIG. 5). The cup points determined for the respective cross sections are connected to obtain the cup rim (Step 13).

Through the above-described method, even if the plane of the disk is inclined, it is possible to detect the cup rim accurately and improve reproducibility as well.

Figure 6:
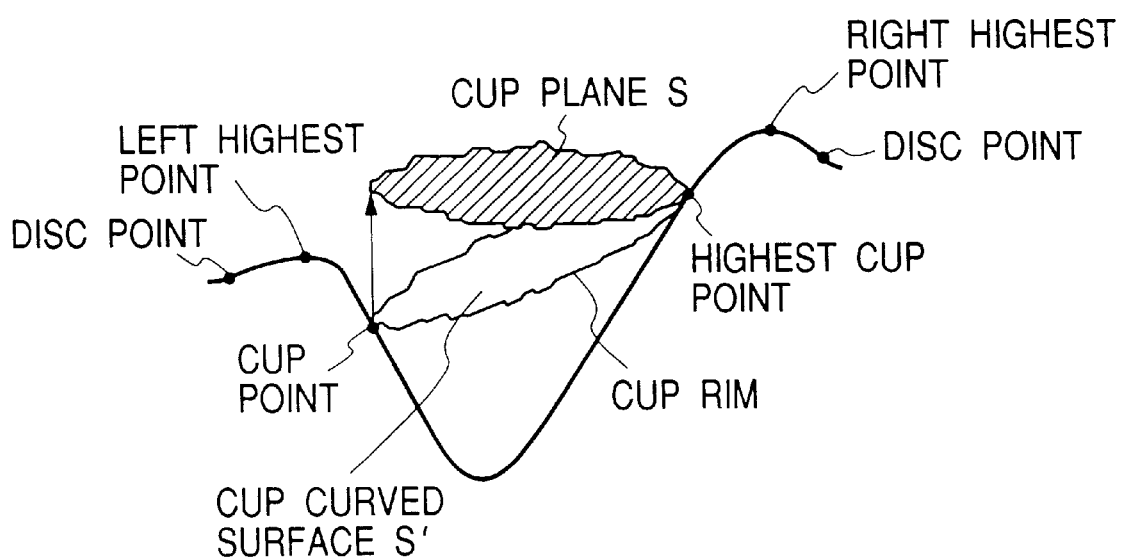
FIG. 6 is a diagram explaining a method for obtaining a cup plane S.

Subsequently, the computing and analyzing unit 2 computes various parameters of the optic disk on the basis of the computed data of the cup. In this embodiment, in the computation of the parameters of the optic disk, as shown in FIG. 6, a cup plane S is obtained by taking a highest point of the cup rim as a reference position and by projecting a curved surface S' of the cup defined by the cup rim onto a horizontal plane (reference plane) including the reference position. The outer peripheral line of this cup plane S is used in computation as the cup rim data.

As the parameters of the optic disk, the following are computed among others: the distance ratio (C/D ratio) between the cup rim and the disk rim, the area (cup area) of the plane within the cup rim, the area ratio (C/D area ratio) between the cup and the disk, the depth of the cup (maximum cup depth), and the cup volume. It should be noted that the parameters of the maximum cup depth and the cup volume are computed by incorporating correction processing in which the values are shifted in correspondence with the cup plane S. The computed parameters of the optic disk are displayed on the display 5, and are stored and recorded.

Through the parameters of the optic disk obtained in the above-described manner, it is possible to quantitatively measure the optic disk, which can be made useful in the diagnosis of glaucoma.

As described above, in accordance with the present invention, it is possible to reduce variations due to errors among operators and repeated analysis, and obtain highly reliable results of analysis. In addition, it is possible to improve the reproducibility of the results of analysis.

What is claimed is:

1. A method for analyzing a stereoscopic image of a fundus to detect and analyze an optic disk on the basis of the stereoscopic image of the fundus, the method comprising:

a first step of designating a disk line in the stereoscopic image of the fundus;

a second step of determining a lowest point in a disk region which is determined by the designated disk line;

a third step of determining a cross section of the disk region at each predetermined angle centering on the lowest point in the disk region;

a fourth step of determining highest points at both ends of a line of longitude on each cross section of the disk region;

a fifth step of setting, as cup points in each cross section, points at levels which are respectively lower from the highest points by a predetermined depth; and a sixth step of forming a cup rim by consecutively connecting the thus set cup points in all cross sections.

2. A method for analyzing a stereoscopic image of a fundus according to claim 1, wherein said second step includes:

a step of determining a first tentative central position in the disk region determined by the disk line designated in said first step;

a step of determining a first cross section of the disk region at each predetermined angle centering on the first tentative central position;

a step of determining a lowest point in each of the first cross sections of the disk region; and a step of determining a lowest point in the disk region among the lowest points determined in the respective first cross sections of the disk region.

3. A method for analyzing a stereoscopic image of a fundus according to claim 2, further comprising:

a step of determining a second cross section of the disk region at each predetermined angle centering on the lowest point in the disk region among the lowest points determined in the respective first cross sections;

a step of determining a lowest point in each of the second cross section of the disk region; and a step of determining a lowest point in the disk region among the lowest points determined in the respective second cross sections of the disk region.

4. A method for analyzing a stereoscopic image of a fundus according to claim 3, wherein the step of determining a second cross section of the disk region is shared with said third step.

5. A method for analyzing a stereoscopic image of a fundus according to claim 1, wherein in said fifth step, if a plurality of points exists at a level lower from one of the highest points by the predetermined depth, then one of the points, which is closest to the lowest point determined in said second step, is set as the cup point.

6. A method for analyzing a stereoscopic image of a fundus according to claim 1, further comprising the step of obtaining a cup plane by taking as a reference position a highest point of the cup rim as a result of comparison of the highest points determined in said fourth step and by projecting a curved surface of the cup defined by the cup rim onto a horizontal plane including the reference position.

7. A method for analyzing a stereoscopic image of a fundus according to claim 1, further comprising the step of computing optic disk parameters.

8. An apparatus for analyzing a stereoscopic image of a fundus, which has storage means for storing the method for analyzing a stereoscopic image of a fundus according to claim 1.

9. An apparatus for analyzing a stereoscopic image of a fundus, which has storage means for storing the method for analyzing a stereoscopic image of a fundus according to claim 2.

10. An apparatus for analyzing a stereoscopic image of a fundus, which has storage means for storing the method for analyzing a stereoscopic image of a fundus according to claim 3.

11. An apparatus for analyzing a stereoscopic image of a fundus, which has storage means for storing the method for analyzing a stereoscopic image of a fundus according to claim 4.

12. An apparatus for analyzing a stereoscopic image of a fundus, which has storage means for storing the method for analyzing a stereoscopic image of a fundus according to claim 5.

13. An apparatus for analyzing a stereoscopic image of a fundus, which has storage means for storing the method for analyzing a stereoscopic image of a fundus according to claim 6.

14. An apparatus for analyzing a stereoscopic image of a fundus, which has storage means for storing the method for analyzing a stereoscopic image of a fundus according to claim 7.

15. A method for analyzing a stereoscopic image of a fundus according to claim 1, wherein said cup points are set on a surface of the fundus within the disk region.

16. An apparatus for analyzing a stereoscopic image of a fundus to detect and analyze an optic disk on the basis of the stereoscopic image of the fundus, the apparatus comprising:

data input means for inputting data on the stereoscopic image of the fundus;

designating means for designating a disk line in the input stereoscopic image of the fundus;

storage means for storing a program for detecting a cup rim on the basis of the designated disk line and the data on the stereoscopic image of the fundus, said program including the steps of determining a lowest point in a disk region which is determined by the designated disk line, determining a cross section of the disk region at each predetermined angle centering on the lowest point, determining highest points at both ends of a line of longitude on each cross section of the disk region, setting, as cup points in each cross section, points existing at levels which are respectively lower from the highest points by a predetermined depth, and forming a cup rim by consecutively connecting the thus set cup points in all cross sections;

program executing means for executing said program;

parameter computing means for computing predetermined parameters for analysis of the optic disk on the basis of the cup rim detected by said program executing means; and display means for displaying a result of the computation.

17. An apparatus for analyzing a stereoscopic image of a fundus to detect and analyze an optic disk on the basis of the stereoscopic image of the fundus, the apparatus comprising:

a data input device which allows input of data on the stereoscopic image of the fundus;

a designating device which allows designation of a disk line in the input stereoscopic image of the fundus;

a storage device which stores a program that detects a cup rim on the basis of the designated disk line and the data on the stereoscopic image of the fundus, said program including the steps of determining a lowest point in a disk region which is determined by the designated disk line, determining a cross section of the disk region at each predetermined angle centering on the lowest point, determining highest points at both ends of a line of longitude on each cross section of the disk region, setting, as cup points in each cross section, points at levels which are respectively lower from the highest points by a predetermined depth, and forming a cup rim by consecutively connecting the thus set cup points in all cross sections;

a program executing device which executes said program;

a parameter computing device which computes predetermined parameters for analysis of the optic disk on the basis of the cup rim detected by said program executing device; and a display which displays a result of the computation.

* * * * *